United States Patent [19]

Ikeda et al.

[11] Patent Number: 5,434,088
[45] Date of Patent: Jul. 18, 1995

[54] METHOD OF AND KIT FOR ENERGY TRANSFER IMMUNOASSAY WITH COLLOIDAL PARTICLES

[75] Inventors: Kenji Ikeda, Yokohama; Kazuhisa Toyoda, Fujisawa; Hideo Suzuki, Yamato, all of Japan

[73] Assignee: Tosoh Corporation, Yamaguchi, Japan

[21] Appl. No.: 248,527

[22] Filed: May 24, 1994

Related U.S. Application Data

[63] Continuation of Ser. No. 760,137, Sep. 16, 1991, abandoned.

[30] Foreign Application Priority Data

Sep. 14, 1990 [JP] Japan .................................. 2-242721

[51] Int. Cl.$^6$ .................. G01N 33/553; G01N 33/542
[52] U.S. Cl. ..................: ...................... 436/525; 435/969; 435/975; 436/164; 436/172; 436/524; 436/531; 436/534; 436/536; 436/537; 436/538; 436/541; 436/800; 436/805
[58] Field of Search ................ 435/969, 975; 436/164, 436/172, 524, 525, 531, 534, 536–538, 541, 800, 805

[56] References Cited

U.S. PATENT DOCUMENTS

| | | | |
|---|---|---|---|
| 4,261,968 | 4/1981 | Ullman et al. | 424/8 |
| 4,486,530 | 12/1984 | David et al. | 435/7 |
| 4,572,901 | 2/1986 | Ceriani et al. | 436/810 |
| 4,654,300 | 3/1987 | Zuk et al. | 435/7 |

FOREIGN PATENT DOCUMENTS

| | | |
|---|---|---|
| 0063852 | 11/1982 | European Pat. Off. . |
| 0092344 | 10/1983 | European Pat. Off. . |
| 0354847 | 2/1990 | European Pat. Off. . |
| 0370561 | 5/1990 | European Pat. Off. . |
| WO87/07385 | 12/1987 | WIPO . |

OTHER PUBLICATIONS

Stryer, "Fluorescence Energy Transfer as a Spectroscopic Ruler", Ann. Rev. Biochem., 1978, 47, pp. 819–846.
Methods in Enzymology vol. 74, No. c, 1981, pp. 29–61 Ullman et al "Fluroescence Excitation Transfer Immunoassay".

Primary Examiner—Toni R. Scheiner
Assistant Examiner—Christopher L. Chin
Attorney, Agent, or Firm—Nixon & Vanderhye

[57] ABSTRACT

A target substance is detected by a sandwich immunoassay using fine particle (A) having bound to it a fluorescer and an antibody reacting specifically with the target substance, and a fine particle (B) having bound to it a quencher and an antibody reacting specifically with the target substance, through a different antigenic determinant. Also disclosed is a competitive immunoassay having a fine particle (C) bound to it a fluorescer or a quencher, and an antibody reacting specifically with the target substance, a bound product (D) composed of the remainder of the fluorescer and the quencher, or a known amount of the target substance. Binding of the fluorescer and the quencher to the fine particle (A), (B) or (C) is affected so that the fluorescer and the quencher are covalently bound to a substance adsorbed on the fine particle. The sandwich immunoassay is advantageously conducted using a kit containing (i) the fluorescer- and antibody-bound fine particle (A) and (ii) the quencher- and antibody-bound fine particle (B). The competitive immunoassay is advantageously conducted by using a kit containing (i) the fluorescer- or quencher- and-the antibody-bound fine particle (C), and (ii) the bound product (D) of the quencher or fluorescer and the target substance.

14 Claims, 3 Drawing Sheets

METHOD OF AND KIT FOR ENERGY TRANSFER IMMUNOASSAY WITH COLLOIDAL PARTICLES

This is a continuation of application Ser. No. 07/760,137, filed Sep. 16, 1991, now abandoned.

BACKGROUND OF THE INVENTION (1) Field of the Invention

This invention relates to a method of the immunoassay, which is applied to the detection of pathogens and disease markers in clinical examinations and to the industrial immunological detection of infinitesimal amounts of target substances. It also relates to a kit for the above-mentioned immunoassay.

(2) Description of the Related Art

The immunoassay using a naturally occuring antibody or an artificially prepared antibody is characterized by a high specificity and a high sensitivity, and is utilized for detecting an infinitesimal amount of a substance. For example, immunoassay is utilized for the clinical examination of detecting disease markers specifically secreted in the case of such diseases as an infectious disease, a tumor, a myocardial infarction and a cerebral thrombosis, or for detecting an infinitesimal amount of a substance in the open air.

As described, for example, in *Enzyme Immunoassay* (Proteins, Nucleic acids and Enzymes, separate volume, No. 31, pages 13–26, published by Kyoritsu Shuppan K. K.), many methods of the immunoassay have recently developed. Of these methods, the latex agglutination method has been utilized from old for the clinical examination because the operation is simple. However, tile kinds of infinitesimal substances to be tested are now increasing and also the number of items requiring such a high sensitivity as not attainable by the latex agglutination method is increasing.

As the method popularly adopted in these days, there can be mentioned the radio-immunoassay (RIA) and the enzyme immunoassay (EIA). RIA is not favorably used inspite of a high-sensitivity performance, because the assay has a large influence on a human body, and EIA utilizing an enzyme reaction instead of using a radioisotope as the labelled substance is more frequently adopted.

From the viewpoint of the simplicity of the detection system, it is desirable to develop the homogeneous process not requiring B/F separation as a substitute for the conventional heterogeneous process. Ullman et al teach that a fluorescent substance or quencher chemicaly bound to a sandwichable antibody can be used for an immunological reaction [Methods in Enzymology, vol. 74, 28 (1981)]. The taught process is a homogeneous process utilizing a principle that when a sandwich is formed by an antigen-antibody reaction, by an approach of the fluorescent substance and quencher bound to the antibodies to each other, the fluorescent energy of the fluorescent substance is shifted to the exciting energy of the quencher, resulting in reduction of the fluorescence intensity of the fluorescent substance.

As described above, the conventional immunological detection method is complicated because many steps such as the B/F separation step are necessary. Moreover, since the antigen-antibody reaction is carried out in a heterogeneous system where the solid phase and the liquid phase are copresent and the enzyme reaction or the like is used at the final stage, a long time is required for the measurement. In the homogeneous process proposed by Ullman et al, since both of the fluorescent substance and the quencher as the labelled substances are fixed to the antibody, there is a risk of drastic reduction of the performance of the antibody and elevation of sensitivity is limited.

SUMMARY OF THE INVENTION

The present inventors have completed the present invention as the result of investigations made with a view to solving the above-mentioned problems.

More specifically, in accordance with one aspect of the present invention, there is provided a method of the immunoassay comprising the steps of:

binding a fluorescent substance and an antibody reacting specifically with a target substance to be detected, to a fine particle (A);

binding a quencher and an antibody reacting specifically with the target substance to be detected, through a different antigen determinant, to a fine particle (B);

placing said fine particle (A) and said fine particle (B) in contact with the target substance contained in a sample to form an immunoreaction product comprising the target substance sandwiched between the antibody on said fine particle (A) and the antibody on said fine particle (B); and detecting a quenching of the fluorescence occurring due to the quencher, thus to measure the target substance in the sample.

In accordace with another aspect of the present invention, there is provided a method of the immunoassay comprising the steps of:

binding one member selected from a fluorescent substance and a quencher, and an antibody reacting specifically with a target substance to be detected to a fine particle (C);

binding the other member selected from the fluorescent substance and the quencher to a known amount of the target substance to form a bound product (D);

placing said antibody-bound fine particle (C) and the bound product (D) in contact with the target substance contained in a sample thereby to competitively react the target substance in the sample and the known amount of the target substance with the antibody on said particle (C), thus forming an immunoreaction product comprising the target substance and the antibody on said particle (C); and (4) detecting a quenching of the fluorescence occurring due to the quencher, thus to measure the target substance in the sample.

In accordance with still another aspect of the present invention, there is provided a kit for the immunoassay comprising a fine particle (A) having bound thereto a fluorescent substance and an antibody reacting specifically with a target substance to be detected, and a fine particle (B) having bound thereto a quencher and an antibody reacting specifically with the target substance through a different antigen determinant.

In accordance with a further aspect of the present invention, there is provided a kit for the immunoassay comprising a fine particle (C) having bound thereto one member selected from a fluorescent substance and a quencher, and an antibody reacting specifically with a target substance to be detected, and a bound product (D) composed of a known amount of the target substance and the other member selected from the fluorescent substance and the quencher.

DETAILED DESCRIPTION OF THE PREFERRED EMBODIMENTS

Figure 1:
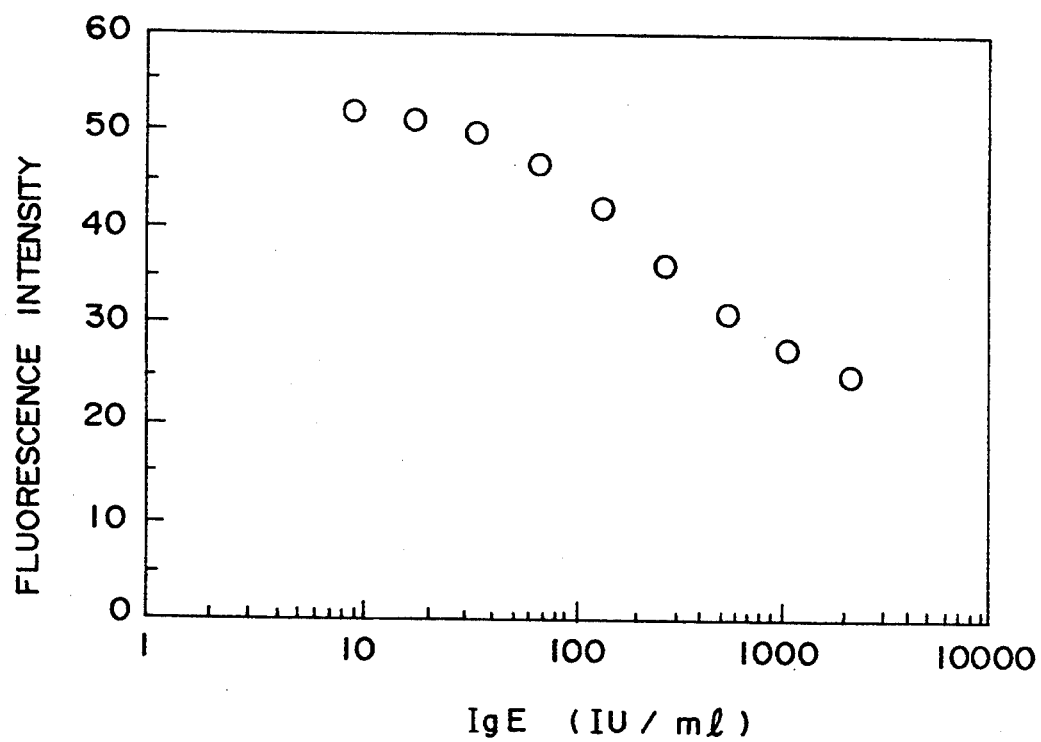
FIG. 1 is a diagram illustrating changes of the fluorescence intensity of fluorescein to the concentration of the IgE antigen in Example 1.

The immunoassay methods and kits of the present invention will be described in detail.

The immunoassay method according to the first aspect of the present invention is now described. The antibody used in the present invention is not particularly limited, as far as it is capable of reacting specifically with a target substance to be detected. Either a monoclonal antibody or a polyclonal antibody may be used. The source material is not particularly limited, and for example, there can be used mouse, rat, sheep, goat, bovine and equine. In the present invention, two kinds of antibodies are used and the reaction is carried out so that the antigen is sandwiched between these two antibodies, and therefore, the two antibodies must be combined so that binding is effected through different antigen determinants. One of the two antibodies is bound together with a fluorescent substance to a fine particle (A), and the other antibody is bound together with a quencher to a fine particle (B).

The size of the fine particles (A) and (B) is larger than the size of the molecule level but cannot be distinguished with the naked eye. For example, various colloidal particles having a diameter of about 10 angstroms to about 5,000 angstroms can be used. More specifically, there can be mentioned polymeric colloids of latexes and synthetic polymers, colloids of noble metals such as platinum, gold and silver, and colloids of inorganic oxides such as aluminum oxide and titanium oxide. A smaller particle diameter is preferable because the fluorescent substance on the fine particle (A) can be approached more closely to the quencher on the fine particle (B).

The binding of the antibody reacting specifically with the target substance to the fine particle (A) or (B) can be carried out by adopting a means customarily used for immunological reactions such as physical adsorption and chemical binding.

The fluorescent substance is bound to a fine particle (A) and the quencher is bound to a fine particle (B). The fluorescent substance and the quencher are not particularly limited, but a preferable fluorescent substance should be selected depending upon the particular quencher. Typical combinations of the fluorescent substance and the quencher include fluorescein and Texas red, pyrene butyrate and $\beta$-phycoerythrin, fluorescein and 4',5'-dimethoxy-6-carboxyfluorescein, and fluorescein and rhodamine. The fluorescent substance and the quencher can be bound either directly or indirectly to the fine particles (A) and (B), respectively. In the indirect binding, BSA, polyethylene glycol (PEG) or another substance is adsorbed on a fine particle (A) or (B) and the fluorescent substance or quencher is bound to this adsorbed substance through a covalent bond. Of these bindings, direct binding is preferable because the preparation is simple.

The thus-prepared fine particle (A) having bound thereto the fluorescent substance and the antibody reacting specifically with the target substance, and the thus-prepared fine particle (B) having bound thereto the quencher and the antibody reacting specifically with the target substance through a different antigen determinant, are placed in contact with the target substnce to be detected in the sample. The order of the contact is not particularly limited, and either of the particles (A) and (B) can be contacted at first or they can be simultaneously contacted with the target substance in the sample.

By this contact, the target substance in the sample is sandwiched between the antibody on the particle (A) and the antibody on the Particle (B) to form an immunoreaction product. Before the immunoreaction is caused, since the fluorescent substance and the quencher are separated from each other, they do not influence each other and they have inherent energies, respectively. However, when an immunoreaction product is produced, the fluorescent substance and the quencher are placed very closely to each other and mutually act on each other, a quenching of the fluorescence occurs due to the quencher. Since the quenching of the fluorescence has a correlation to the amount of the immunological reaction product, the target substance contained in the sample can be determined by measuring the degree of quenching.

The immunoassay method according to the second aspect of the present invention will now be described. The same antibody, fine particles, fluorescent substance and quencher as described above with respect to the first aspect of the present invention can be used. Moreover, binding of the antibody, fluorescent substance and quencher to the fine particles can be performed by the same procedure. However, in the second aspect of the present invention, only the fine particle (C) having bound thereto an antibody reacting specifically with a target substance and one of the fluorescent substance and the quencher are used.

Either of the fluorescent substance and the quencher can be bound onto the fine particle (C), but preferably the quencher is bound onto the particle (C). The reason is that the labelled substance can be bound onto the fine particle (C) in an amount larger than the amount bound onto the target substance, and the sensivity is improved.

The other substance selected from the fluorescent substance and the quencher is bound to a known amount of the target substance. Either direct binding or indirect binding through a particle or a polymer can be adopted.

The fine particle (C) to which the antibody and one of the fluorescent substance and quencher are bound and the known amount of the target substance to which the other substance selected from the fluorescent substance and the quencher is bound are placed into contact with the target substance in a sample to effect a competitive reaction, whereby an immunoreaction product comprising the target substance and the antibody on the particle (C), is produced. Before the immunoreaction is caused, the fluorescent substance and the quencher on the particle (C) and the known amount of the target substance are separated from each other, and therefore, they do not influence each other and they exhibit inherent energies, respectively. However, once an immunoreaction is caused, the fluorescent substance and the quencher mutually act on each other and the energy states are changed, and a quenching of the fluorescence occurs. Since quenching of the fluorescence has a correlation to the quantity of the immunoreaction product, the target substance contained in the sample can be determined by measuring the degree of quenching.

According to the present invention, there are provided kits to be used for the above-mentioned two methods of the immunoassay.

The kit used for the first immunoassay comprises a fine particle (A) having bound thereto a fluorescent substance and an antibody reacting specifically with a target substance to be detected, and a fine particle (B) having bound thereto a quencher and an antibody reacting specifically with the target substance through a different antigen determinant.

The kit used for the second immunoassay comprises a fine particle (C) having bound thereto one member selected from a fluorescent substance and a quencher, and an antibody reacting specifically with a target substance to be detected, and a bound product (D) composed of a known amount of the target substance and the other member selected from the fluorescent substance and the quencher.

Respective components constituting these kits are the same as those described above with respect to the immunoassay methods. Furthermore, reagents having no baneful influences on the immunoassay, such as a diluent and a stabilizer, can be incorporated in the kits.

The present invention will now be described in detail with reference to the following examples that by no means limit the scope of the invention.

EXAMPLE 1

Synthesis of Fine Particle (A) Having Bound Thereto Fluorescein and Antibody and Fine Particle (B) Having Bound Thereto Rhodamine and Antibody Two kinds of anti-IgE monoclonal antibodies recognizing different sites, respectively, were fixed to polystyrene latexes A and B having bound thereto fluorescein as the fluorescent substance and rhodamine as the quencher, respectively. More specifically, 100 g of monomeric styrene was dissolved in 500 g of water, and 10 g of SDS was added to the solution and the mixture was stirred and heated. At about 60° C., potassium persulfate was added in an amount of 0.4 g per 100 ml of water to initiate polymerization. The reaction mixture was stirred for three hours and then cooled to stop the reaction. The thus-obtained latex solution was dialyzed for 1 day with pure water. Then 200 mg of fluorescein or rhodamine was added into 10 ml of the obtained 1% solution of the polystyrene latex, and the mixture was treated for 30 minutes by an ultrasonic dispersing device. The obtained solution was dialysed for 1 day with pure water, and thus, the fluorescein- or rhodamine-bound polystyrene latex was obtained.

Then 500 μl of a buffer solution containing 0.1M of sodium bicarbonate, 0.15M of sodium chloride and 0.08% by weight of sodium azide (the pH value was 8.5) was mixed with 500 ul of the fluorescein-bound polystyrene latex (100 times dilution with water), and 4 ml of pure water was further added. Then 40 μl of anti-IgE monoclonal antibody (the antibody concentration was 10 mg/ml) was added to the mixture, and the mixture was stirred. Then 5 ml of 10% polyethylene glycol having a molecular weight of 20,000 was added to the polystyrene latex, and the mixture was allowed to stand for 1 hour to effect blocking. Thus an antibody- and fluorescein-bound polystyrene latex was obtained. Reaction was carried out in the same manner as dscribed above by using the rhodamine-bound polystyrene latex and anti-IgE monoclonal antibody recognizing a different site, whereby an antibody- and rhodamine-bound polystyrene latex was obtained.

Detection of IgE Antigen Concentration

To 50 μpl of each of the fluorescent substance- and antibody-bound latex solution and the quencher- and antibody-bound latex was added 900 μl of standard serum containing 10 to 2,200 IU/ml of IgE antigen as a sample, and incubation was conducted for 10 minutes. Then the fluorescence intensity was measured at an exciting wavelength of 495 nm (the band path was 5 nm) and a flurescence wavelength of 515 nm (the band path was 5 nm) by a fluorescence spectrophotometer. The thus-obtained results are shown in FIG. 1. As is seen from FIG. 1, it was confirmed that the fluorescence intensity was reduced with an increase of the amount of the antigen, and the IgE antigen concentration could be detected from the degree of reduction of the fluorescence intensity.

EXAMPLE 2

Synthesis of Fine Particle (A) Having Bound Thereto Fluorescein Isothocyanate/BSA and Antibody and Fine Particle (B) Having Bound Thereto Rhodamine Isothiocyanate/BSA and Antibody BSA having bound thereto fluorescein isothiocyanate as the fluorescent substance and BSA having bound thereto rhodamine isothiocyanate as the quencher were fixed respectively to polyethylene latexes having fixed thereto respectively two kinds of anti-FSH monoclonal antibodies recognizing different sites. More specifically, 20 mg of fluorescein isothiocyanate (FITC) was added into 100 ml of PBS buffer containing 100 mg of BSA, and the mixture was stirred for 24 hours and dialyzed for 24 hours to obtain FITC-fixed BSA. Separately, 20 mg of rhodamine isothiocyanate (TMRITC) was added into 100 ml of PBS buffer containing 100 mg of BSA, and the mixture was stirred for 24 hours and dialyzed for 24 hours to obtain TMRITC-fixed BSA.

Separately, 500 μl of a buffer solution containing 0.1M of sodium bicarbonate, 0.15M of sodium chloride and 0.08% by weight of sodium azide (the pH value was 8.5) was mixed with 500 pl of a 1% by weight polystyrene latex solution prepared in the same manner as in Example 1, and 4 ml of pure water was further added. Then 50 μl of anti-FSH monoclonal antibody (the antibody concentration was 0.1 mg/ml) was added, and the mixture was stirred. Then 50 μl of the above-mentioned FITC-fixed BSA was further added to the mixture, and the mixture was allowed to stand for 1 hour to effect blocking, whereby an FITC- and antibody-fixed latex was obtained.

A similar treatment was carried out by using anti-FSH monoclonal antibody recognizing a different site and TMRITC-fixed BSA to obtain a TMRITC- and antibody-fixed latex.

Detection of FSH Antigen Concentration

Figure 2:
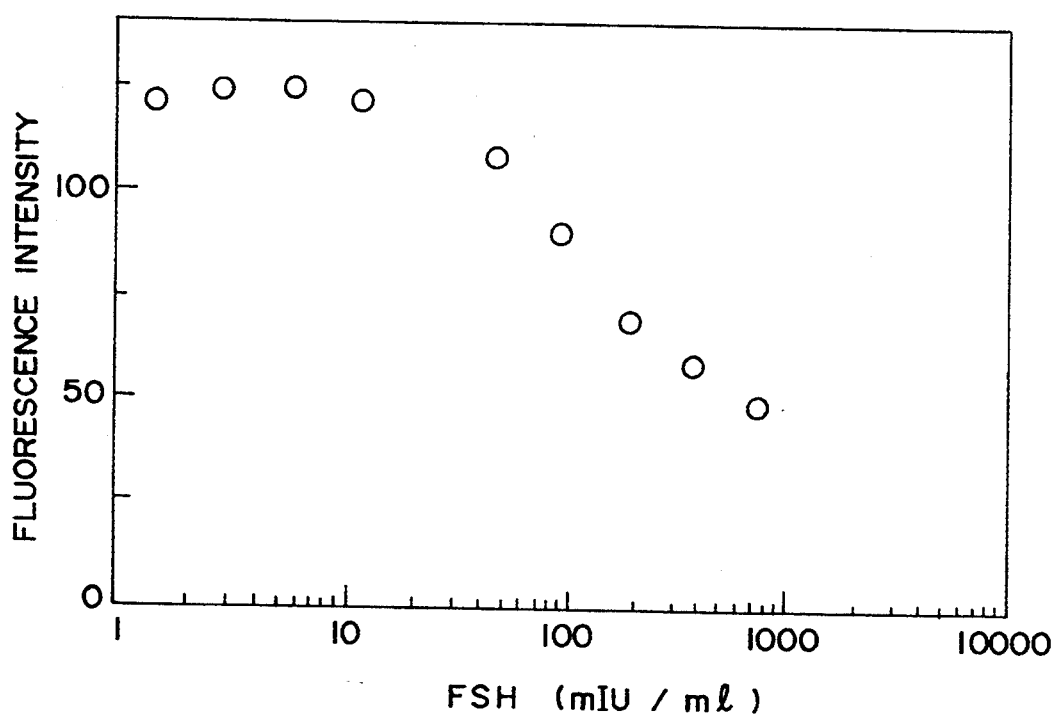
FIG. 2 is a diagram illustrating changes of the fluorescence intensity of fluorescein to the concentration of the FSH antigen of Example 2.

To 50 μl of each of the thus-obtained FITC- and antibody-fixed latex solution and the TMRITC- and antibody-fixed latex solution was added 900 μl of standard serum containing 1 to 1,000 mIU/ml of FSH antigen as a sample, and incubation was conducted for ten minutes. The fluorescence intensity was measured at an exciting wavelength of 495 nm (the band path was 5 nm) and a fluorescence wavelength of 515 nm (the band path was 5 nm) by a fluorescence spectrophotometer. The thus-obtained results are shown in FIG. 2. As is seen from FIG. 2, it was confirmed that the fluorescence intensity was reduced with an increase of the amount of the antigen, and the concentration of the FSH antigen could be detected from the degree of reduction of the fluorescence intensity.

EXAMPLE 3

Synthesis of Fine Particle (A) Having Bound Thereto FITC/BSA and Antibody and Fine Particle (B) Having Bound Thereto TMRITC/BSA and Antibody BSA having bound thereto fluorescein isothiocyanate (FITC) as the fluorescent substance and BSA having bound thereto rhodamine isothiocyanate (TMRITC) as the quencher were fixed respectively to platinum fine particles to which two kinds of anti-FSH monoclonal antibodies recognizing different sites were fixed respectively.

Namely, FITC-fixed BSA and TMRITC-fixed BSA were obtained in the same manner as described in Example 2.

Separately, 500 μl of a buffer solution containing 0.1M of sodium bicarbonate, 0.15M of sodium chloride and 0.08% by weight of sodium azide (the pH value was 8.5) was mixed with 500 1μl of a solution of platinum fine particles synthesized according to the conventional method (Chemistry and Applications of Noble Metals, pages.60–71, Kodansha K. K.) and 4 ml of pure water was further added. Then 50 μl of anti-FSH monoclonal antibody (the antibody concentration was 0.1 mg/ml) was added to the mixture, and the mixture was stirred. Then 50 μl of the above-mentioned FITC-fixed BSA was added to the mixture, and the mixture was allowed to stand for 1 hour to obtain FITC and antibody-fixed platinum particles. A similar treatment was carried out by using anti-FSH monoclonal antibody recognizing a different site and TMRITC-fixed BSA to obtain TMRITC- and antibody-fixed platinum fine particles.

Detection of FSH Antigen Concentration

Figure 3:
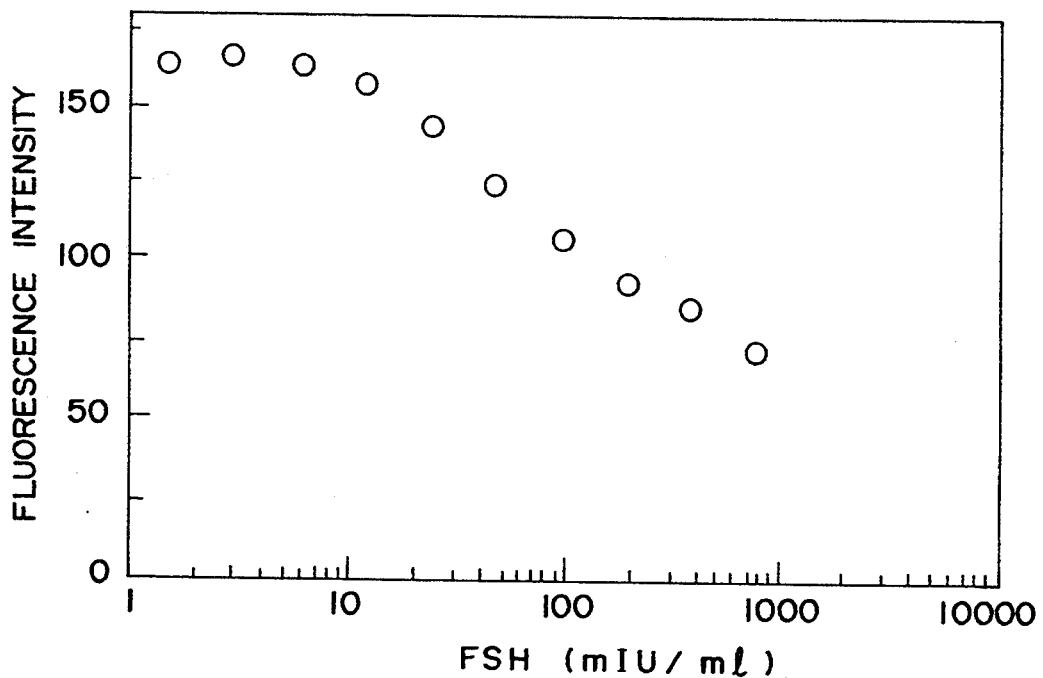
FIG. 3 is a diagram illustrating changes of the fluorescence intensity of fluorescein to the concentration of the FSH antigen in Example 3.

To 50 μl of the thus-obtained FITC- and antibody-fixed platinum fine particle solution and the TMRITC- and antibody-fixed platinum fine particle solution was added 900 μl of standard serum containing 1 to 1,000 mIU of FSH antigen as a sample, and incubation was carried out for 10 minutes. Then the fluorescence intensity was measured at an exciting wavelength of 495 nm (the band path was 5 nm) and a fluorescence wavelength of 515 nm (the band path was 5 nm) by a fluorescence spectrophotometer. The results are shown in FIG. 3. As is seen from FIG. 3, it was confirmed that the fluorescent intensity was reduced with an increase of the amount of the antigen, and the FSH antigen concentration could be detected from the degree of reduction of the fluorescence intensity.

EXAMPLE 4

Synthesis of Fine Particle (A) having Bound Thereto FITC and Antibody and Fine Particle (B) Having Bound Thereto TMRITC and Antibody In the same manner as described in Example 3, a fine platinum particle having bound thereto TMRITC and an anti-FSH monoclonal antibody and a fine platinum particle having bound thereto FITC and an anti-FSH monoclonal antibody recognizing a different antigen site were prepared.

Detection of FSH Antigen Concentration

Figure 4:
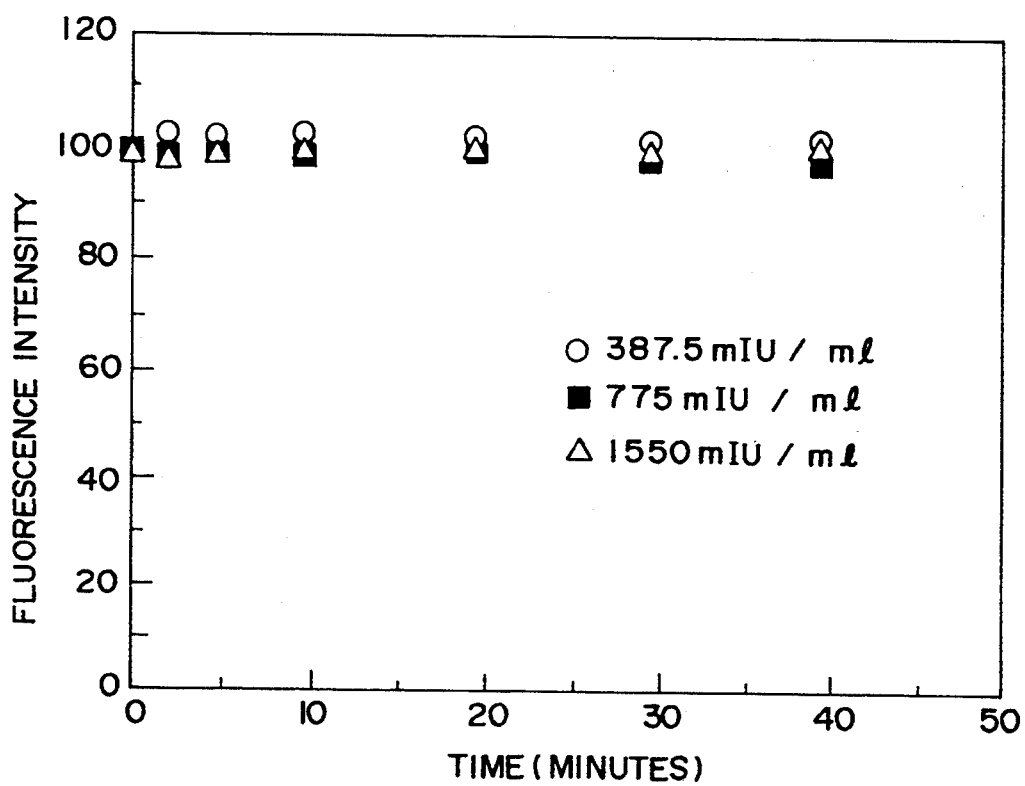
FIG. 4 is a diagram illustrating the relationship of the relative fluorescence intensity to the incubation time in Example 4; and, FIG. 5 is a diagram illustrating changes of the fluorescence intensity of fluorescein to the avidin antigen concentration in Examples 5 and 6.

The measurement was carried out in the same manner as described in Example 3 except that standard serum containing 387.5 mIU/ml, 775mIU/ml or 1,550 mIU/ml of FSH antigen was used, and the advance of the reaction was examined while adjusting the incubation time to 0.5, 2, 5, 10, 20, 30 or 40 minutes. The results are shown in FIG. 4. In FIG. 4, the incubation time is plotted on the abscissa and the relative fluorescence intensity, calculated based on the supposition that the fluorescence intensity obtained at 0.5 minute's incubation is 100, is plotted on the ordinate. As is seen from FIG. 4, even if the incubation time was short, the reaction was sufficiently advanced. Therefore, it was found that the time required for the detection can be drastically shortened.

EXAMPLE 5

Synthesis of Fine Particle (C) Having Bound Thereto TMRITC/BSA and Antibody

BSA having bound thereto TMRITC as the quencher was fixed to a latex having fixed thereto an anti-avidin antibody. More specifically, 100 μl of a 1/100 dilution of a latex of the reagent class supplied by Sekisui Chemical Co. (the particle size was 0.525 pm and the solid content of 10% by weight) was added to 4.9 ml of 0.1M tris-hydrochloric buffer having a pH value of 8.0, and 50 μl of an anti-avidin antibody (supplied by EY Laboratory, 7.5 mg/ml) was further added to bind it to the latex particles.

To the antibody-fixed latex particles was added 50 μl of TMRITC-fixed BSA obtained in the same manner as in Example 2, and reaction was carried out for 2 hours. Then 500 μl of 10% polyethylene glycol having a molecular weight of 20,000 was added to the reaction mixture and blocking was conducted for 1 hour, whereby an antibody- and TMRITC-fixed latex was prepared.

Detection of Avidin Concentration

Figure 5:
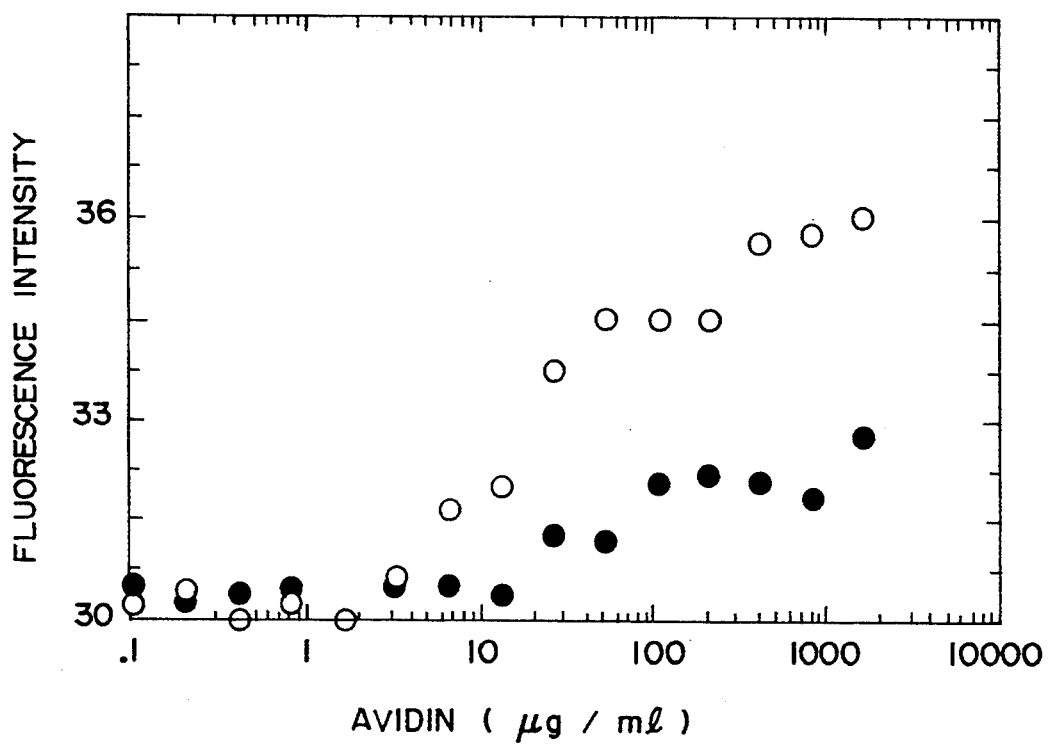

To a microtiter plate for the fluorometry were added 50 μl of avidin (supplied by Nakarai Tesque, 0.1 ug/ml to 1,000 μg/ml), 50 ul of FITC-labelled avidin (supplied by Cappel, 0.0259 mg/ml) and 100 μl of the antibody- and TMRITC-fixed latex. Incubation was conducted for 0.5 to 60 minutes, and the fluorescence intensity was measured at an exciting wavelength of 495 nm (the band path was 5 nm) and a fluorescence wavelength of 515 nm (the band path was 5 nm) by a microtiter fluorescence reader. The results are shown by white spots in FIG. 5. As is seen from FIG. 5, it was confirmed that the fluorescence was elevated with an increase of the amount of the antigen, and the avidin concentration could be detected with the degree of this increase.

EXAMPLE 6

Synthesis of Fine Particle (C) Having Bound Thereto TMRITC/BSA and Antibody

BSA having bound thereto TMRITC as the quencher was fixed to ultrafine platinum particles having fixed thereto an anti-avidin antibody. More specifically, 120 ml of 1% by weight citric acid (supplied by Wako Junyaku) and 60 ml of chloroplatinic acid ($H_2PtCl_6$ $6H_2O$ supplied by Wako Junyaku) were added into 960 ml of water maintained at 100° C., and the mixture was refluxed and stirred for 3 hours. The mixture was cooled on an ice bath and passed through an ion exchange resin column packed with Amberlite MB-1. It was confirmed that the electric conductivity after the passage through the column was not larger than 5 μS/cm.

To 1 ml of the thus-prepared solution of ultrafine platinum particles was added 4.0 ml of 0.1M tris-hydrochloric acid buffer having a pH value of 8.0, and 50 μl of an anti-avididin antibody (7.5 mg/ml) was added to the mixture to fix the antibody to the platinum particles. Then 50 μl of TMRITC-fixed BSA prepared in the same manner as described in Example 2 was added to the antibody-fixed platnum particles, and reaction was carried out for 2 hours. Then 500 μl of 10% by weight polyethylene glycol having a molecular weight of 20,000 was added to the reaction mixture and blocking was conducted for 1 hour. Thus, antibody- and TMRITC-fixed platinum particles were obtained.

Detection of Avidin Concentration

The measurement was carried out in the same manner as described in Example 5 except that the antibody- and TMRITC-fixed ultrafine platinum particles were used instead of the antibody- and TMRITC-fixed latex. The results are shown by black spots in FIG. 5. As is seen from FIG. 5, it was confirmed that the fluorescence intensity was elevated with an increase of the amount of the antigen, and the avidin concentration.

According to the present invention, a fluorescent substance and a quencher are bound not to an antibody but to fine particles. Therefore, the following effects are attained.

The amounts of the bound fluorescent substance and quencher can be prominently increased, and therefore, detection can be performed at a high sensitivity. The fluorescent substance and the quencher do not inhibit the antigen-antibody reaction, and therefore the antibody is not deactivated.

Since the reaction is conducted in a uniform system, that is, in a liquid phase, there is no need of conducting a complicated operation, such as B/F separation, which is conducted in the conventional method in a solid-liquid heterogeneous system. The time required for the immunoassay, which is about 1 hour in the conventional technique, can be drastically shortened. When the kit for the immunoassay of the present invention is used, the immunoassay can be conveniently effected in a simplfied manner.

What is claimed is:

1. An immunoassay method comprising the steps of:
    binding a fluorescent substance and an antibody reacting specifically with a target substance to the fine particle (A) being effected so that the fluorescent substance is covalently bound to BSA or polyethylene glycol (PEG) which is adsorbed on the fine particle (A) and said antibody being directly bound to the fine particle (A);
    binding a quencher and an antibody reacting specifically with the target substance to be detected, through a different antigenic determinant, to a fine particle (B), said binding of the quencher to the fine particle (B) being effected so that the quencher is covalently bound to BSA or polyethylene glycol (PEG) which is adsorbed on the fine particle (B);
    placing said fine particle (A) and said fine particle (B) in contact with the target substance contained in a sample to give an immunoreaction product comprising the target substance sandwiched between the antibody on said fine particle (A) and the antibody on said fine particle (B); and
    detecting a quenching of the fluorescence occurring due to the quencher, thereby measuring the target substance in the sample.

2. The method of the immunoassay according to claim 1, wherein the fine particles (A) and (B) have a particle diameter of about 10 to 5,000 angstroms and are selected from the group consisting of polymeric colloids, noble metal colloids and inorganic oxide colloids.

3. The method of the immunoassay according to claim 1, wherein a combination of the fluorescent substance and the quencher is selected from the group consisting of a combination of fluorescein and Texas red, a combination of pyrene butyrate and β-phycoerythrin, a combination of fluorescein and 4',5'-dimethoxy-6-carboxyfluorescein, and a combination of fluorescein and rhodamine.

4. An immunoassay method comprising the steps of:
    binding one member selected from the group consisting of a fluorescent substance and a quencher, and an antibody reacting specifically with a target substance to be detected, to a fine particle (C), said binding of the fluorescent substance or the quencher to the fine particle (C) being effected so that the fluorescent substance or the quencher is covalently bound to BSA or polyethylene glycol (PEG) which is adsorbed on the fine particle (C) and said antibody being directly bound to the fine particle (C);
    binding the other member selected from the group consisting of a fluorescent substance and a quencher to a known amount of the target substance to give a bound product (D);
    placing said antibody-bound fine particle (C) and the bound product (D) in contact with the target substance contained in a sample thereby to competitively react the target substance in the sample and the known amount of the target substance with the antibody on said particle (C), thus giving an immunoreaction product of the target substance on the bound product (D) with the antibody on said particle (C); and
    detecting a quenching of the fluorescence occurring due to the quencher, thereby measuring the target substance in the sample.

5. The method of the immunoassay according to claim 4, wherein the quencher is covalently bound to the BSA or polyethylene glycol (PEG) on fine particle (C); and the fluorescent substance is bound to the known amount of the target substance to give the bound product (D).

6. The method of the immunoassay according to claim 4, wherein the fine particle (C) has a particle diameter of about 10 to 5,000 angstroms and is selected from the group consisting of polymeric colloids, noble metal colloids and inorganic oxide colloids.

7. The method of the immunoassay according to claim 4, wherein a combination of the fluorescent substance and the quencher is selected from the group consisting of a combination of fluorescein and Texas red, a combination of pyrene butyrate and β-phycoerythrin, a combination of fluorescein and 4',5'-dimethoxy-6-carboxyfluorescein, and a combination of fluorescein and rhodamine.

8. An immunoassay kit comprising a fine particle (A) having bound thereto a fluorescent substance and an antibody reacting specifically with a target substance to be detected, and a fine particle (B) having bound thereto a quencher and an antibody reacting specifically with the target substance through a different antigen determinant, said antibody being directly bound to the fine particle (B); said fluorescent substance being covalently bound to the fine particle (B); said fluorescent substance being covalently bound top BSA or polyethylene glycol (PEG) which is adsorbed on the fine particle (A), and said quencher being covalently bound to BSA or polyethylene glycol (PEG) which is adsorbed on the fine particle (B).

9. The kit for the immunoassay according to claim 8, wherein the fine particles (A) and (B) have a particle diameter of about 10 to 5,000 angstroms and are selected from the group consisting of polymeric colloids, noble metal colloids and inorganic oxide colloids.

10. The kit for the immunoassay according to claim 8, wherein a combination of the fluorescent substance and the quencher is selected from the group consisting of a combination of fluorescein and Texas red, a combination of pyrene butyrate and β-phycoerythrin, a combination of fluorescein and 4′,5′-dimethoxy-6-carboxyfluorescein, and a combination of fluorescein and rhodamine.

11. An immunoassay kit comprising a fine particle (C) having bound thereto one member selected from the group consisting of a fluorescent substance and a quencher, and an antibody reacting specifically with a target substance to be detected, said antibody being directly bound to the fine particle (C); and a bound product (D) composed of a known amount of the target substance bound to the other member selected from the group consisting of the fluorescent substance and the quencher, said fluorescent substance or said quencher being covalently bound to BSA or polyethylene glycol (PEG) which is adsorbed on the fine particle (C).

12. The kit for the immunoassay according to claim 11, wherein the the quencher is covalently bound to the BSA or polyethylene glycol (PEG) on fine particle (C), and the bound product (D) is composed of the known amount of the target substance bound to the fluorescent substance.

13. The kit for the immunoassay according to claim 11, wherein the fine particle (C) has a particle diameter of about 10 to 5,000 angstroms and is selected from the group consisting of polymeric colloids, noble metal colloids and inorganic oxide colloids.

14. The kit for the immunoassay according to claim 11, wherein a combination of the flurescent substance and the quencher is selected from the group consisting of a combination of fluorescein and Texas red, a combination of pyrene butyrate and β-phycoerythrin, a combination of fluorescein and 4′,5′-dimethoxy-6-carboxyfluorescein, and a combination of fluorescein and rhodamine.

* * * * *